(12) United States Patent
Takahashi et al.

(10) Patent No.: US 6,828,368 B2
(45) Date of Patent: Dec. 7, 2004

(54) BIS(CIS-3,3,5-TRIMETHYLCYCLOHEXYL) PHTHALATE, PROCESS FOR PRODUCING THE SAME, AND THERMOPLASTIC RESIN COMPOSITION

(75) Inventors: Ikuo Takahashi, Kobe (JP); Tomohiro Hashizume, Himeji (JP); Kazuhiro Nakanishi, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 62 days.

(21) Appl. No.: 10/069,886

(22) PCT Filed: Jun. 27, 2001

(86) PCT No.: PCT/JP01/05503

§ 371 (c)(1),
(2), (4) Date: Mar. 1, 2002

(87) PCT Pub. No.: WO02/02502

PCT Pub. Date: Jan. 10, 2002

(65) Prior Publication Data

US 2002/0193482 A1 Dec. 19, 2002

(30) Foreign Application Priority Data

Jul. 3, 2000 (JP) ........................................ 2000-201628

(51) Int. Cl.$^7$ ............................ C09K 15/06; C08K 5/09

(52) U.S. Cl. ............................ 524/285; 252/407; 560/3

(58) Field of Search ...................... 524/285; 252/407; 560/3

(56) References Cited

FOREIGN PATENT DOCUMENTS

| JP | 2000-53874 | 2/2000 |
|----|------------|--------|
| JP | 2001-234151 A | 8/2001 |
| WO | 99/50356 A1 | 10/1999 |

OTHER PUBLICATIONS

Peppiatt et al, "CycloHexane Derivatives. Part I" Howards of Ilford, Ltd., Ilford, Essex, UK, Journal of the Chemical Society, Abstracts, Jul. 1955, pp. 3122–3125.*
Peppiatt et al., J. Chem. Soc. (1955) 3122–3125.

* cited by examiner

*Primary Examiner*—Kriellion A. Sanders
(74) *Attorney, Agent, or Firm*—Birch, Stewart, Kolasch & Birch, LLP

(57) ABSTRACT

Bis(cis-3,3,5-trimethylcyclohexyl) phthalate includes stereoisomers represented by following Formulae (1), (2) and (3) and satisfies the following conditions:

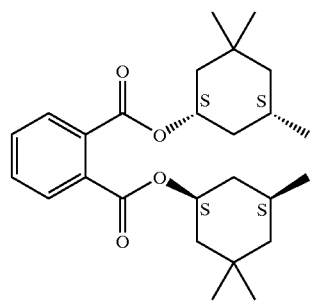

(1)

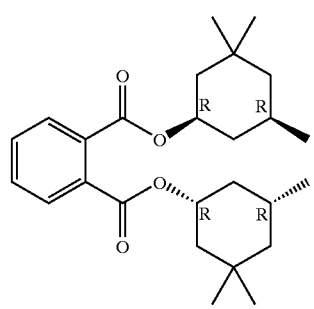

(2)

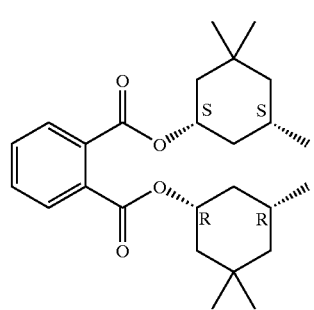

(3)

$a + b + c = 100$, and $50 < a + b$ or $50 < c$ wherein a, b and c are mole percentages of the stereoisomers represented by Formulae (1), (2) and (3), respectively.

The bis(cis-3,3,5-trimethylcyclohexyl) phthalate can be obtained by allowing cis-3,3,5-trimethylcyclohexanol to react with phthalic acid or its reactive derivative and purifying the resulting mixture of stereoisomers, for example, by crystallization.

The bis(cis-3,3,5-trimethylcyclohexyl) phthalate is useful for the preparation of a heat-sensitive tacky adhesive having excellent adhesive strength and blocking resistance.

26 Claims, No Drawings

BIS(CIS-3,3,5-TRIMETHYLCYCLOHEXYL) PHTHALATE, PROCESS FOR PRODUCING THE SAME, AND THERMOPLASTIC RESIN COMPOSITION

This application is the national phase under 35 U.S.C. §371 of PCT International Application No. PCT/JP01/05503 which has an International filing date of Jun. 27, 2001, which designated the United States of America.

TECHNICAL FIELD

The present invention relates to bis(cis-3,3,5-trimethylcyclohexyl) phthalate comprising three stereoisomers in a specific proportion and a preparation process therefor, dl-bis(cis-3,3,5-trimethylcyclohexyl) phthalate, an optically active bis(cis-3,3,5-trimethylcyclohexyl) phthalate and a preparation process therefor, meso-bis(cis-3,3,5-trimethylcyclohexyl) phthalate, as well as to a thermoplastic resin composition and a heat-sensitive tacky adhesive each containing the bis(cis-3,3,5-trimethylcyclohexyl) phthalate as a solid plasticizer, a heat-sensitive tacky adhesive sheet using the heat-sensitive tacky adhesive and a production process therefor.

The bis(cis-3,3,5-trimethylcyclohexyl) phthalate comprising three stereoisomers in a specific proportion, dl-bis(cis-3,3,5-trimethylcyclohexyl) phthalate and meso-bis(cis-3,3,5-trimethylcyclohexyl) phthalate are useful as additives for delayed tack adhesives (heat-sensitive tacky adhesives), hot-melt adhesives, thermal transfer receiving materials, photosensitizers for color photography, hot-melt ink-jet inks, vibration absorbing materials, pencil lead, and vinyl chloride resin compositions, as well as plasticizers or stabilizers for lubricating oils and heating media. The optically active bis(cis-3,3,5-trimethylcyclohexyl) phthalate is useful, for example, as optically resolving agents and intermediate materials for pharmaceutical products and other fine chemicals.

BACKGROUND ART

Bis(3,3,5-trimethylcyclohexyl) phthalate can be used as a solid plasticizer in heat-sensitive tacky adhesives for use in "delayed tack" labels. For example, Japanese Unexamined Patent Application Publication No. 2000-53874 discloses a thermoplastic resin composition comprising a thermoplastic resin and bis (3,3,5-trimethylcyclohexyl) phthalate including a trans-isomer and a cis-isomer in a weight ratio of the former to the latter of 0/100 to 40/60 and mentions that this composition can be used as a heat-sensitive tacky adhesive. The literature also mentions that a heat-sensitive tacky adhesive sheet comprising a heat-sensitive tacky adhesive including bis(cis-3,3,5-trimethylcyclohexyl) phthalate (melting point: 93° C.) as a solid plasticizer has more excellent blocking resistance and adhesive strength than conventional heat-sensitive tacky adhesive sheets comprising dicyclohexyl phthalate as a solid plasticizer. However, demands have been made in some applications on solid plasticizers that can further improve blocking resistance and adhesive strength or solid plasticizers that have further highly durable adhesive strength and transparency.

E. G. Peppiatt and R. J. Wicker have reported the physicochemical properties of bis(3,3,5-trimethylcyclohexyl) phthalate and have mentioned that bis(cis-3,3,5-trimethylcyclohexyl) phthalate has a melting point of 93° C. and bis (trans-3,3,5-trimethylcyclohexyl) phthalate has a melting point of 57° C., in J. Chem. Soc., (1955) 3122. There is no report referring to the physicochemical properties, specifically the relationship between its three-dimensional structure and melting point and other properties, other than the above report.

DISCLOSURE OF INVENTION

Accordingly, an object of the present invention is to provide bis(cis-3,3,5-trimethylcyclohexyl) phthalate, a preparation process therefor and a thermoplastic resin composition that are useful for the preparation of a heat-sensitive tacky adhesive having excellent adhesive strength and blocking resistance.

Another object of the present invention is to provide bis (cis-3,3,5-trimethylcyclohexyl) phthalate, a preparation process therefor and a thermoplastic resin composition that are useful for the preparation of a heat-sensitive tacky adhesive having highly durable adhesive strength and transparency.

A further object of the present invention is to provide a novel stereoisomer of bis(cis-3,3,5-trimethylcyclohexyl) phthalate.

Yet another object of the present invention is to provide a novel optically active bis(cis-3,3,5-trimethylcyclohexyl) phthalate and a preparation process therefor.

Another object of the present invention is to provide a heat-sensitive tacky adhesive and a heat-sensitive tacky adhesive sheet that have excellent blocking resistance and/or adhesive strength and a preparation process for the heat-sensitive tacky adhesive sheet.

A further object of the present invention is to provide a heat-sensitive tacky adhesive and a heat-sensitive tacky adhesive sheet that can sustain high adhesive strength and transparency over a long period of time.

After intensive investigations to achieve the above objects, the present inventors have reveals that bis (cis-3,3,5-trimethylcyclohexyl) phthalate obtained by the reaction between cis-3,3,5-trimethylcyclohexanol and phthalic acid or a reactive derivative thereof includes three stereoisomers and have found that, when the compound comprising the three stereoisomers in a specific proportion is used as a solid plasticizer of a heat-sensitive tacky adhesive, the resulting heat-sensitive tacky adhesive has markedly improved properties such as blocking resistance, adhesive strength and transparency, and that the optical resolution of a mixture of the stereoisomers of bis(cis-3,3,5-trimethylcyclohexyl) phthalate can yield an optically active bis(cis-3,3,5-trimethylcyclohexyl) phthalate. The present invention has been accomplished based on these findings.

Specifically, the present invention provides, in an aspect, bis(cis-3,3,5-trimethylcyclohexyl) phthalate comprising stereoisomers represented by following Formulae (1), (2) and (3) and satisfying the following conditions:

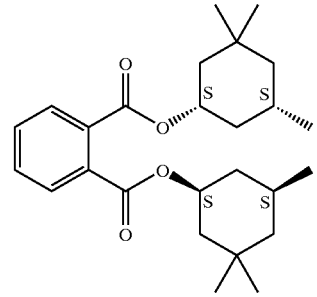

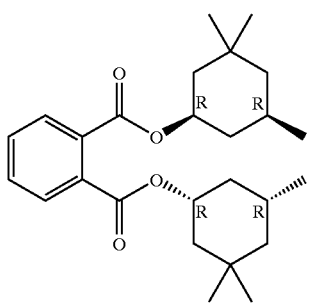

(2)

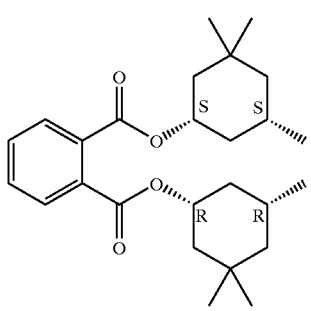

(3)

a + b + c = 100, and 50 < a + b or 50 < c wherein a, b and c are mole percentages of the stereoisomers represented by Formulae (1), (2) and (3), respectively.

The present invention provides, in another aspect, a process for the preparation of bis(cis-3,3,5-trimethylcyclohexyl) phthalate, comprising the steps of allowing cis-3,3,5-trimethylcyclohexanol to react with phthalic acid or a reactive derivative thereof and purifying the resulting mixture of stereoisomers of bis(cis-3,3,5-trimethylcyclohexyl) phthalate to thereby yield bis(cis-3,3,5-trimethylcyclohexyl) phthalate comprising stereoisomers represented by Formulae (1), (2) and (3) and satisfying the following conditions:

$a+b+c=100$, and $50<a+b$ or $50<c$ wherein a, b and c are mole percentages of the stereoisomers represented by Formulae (1), (2) and (3), respectively.

The mixture of stereoisomers of bis(cis-3,3,5-trimethylcyclohexyl) phthalate is purified, for example, by crystallization.

The present invention further provides dl-Bis(cis-3,3,5-trimethylcyclohexyl) phthalate comprising a compound represented by following Formula (1) and a compound represented by following Formula (2):

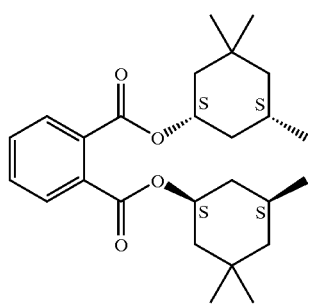

(1)

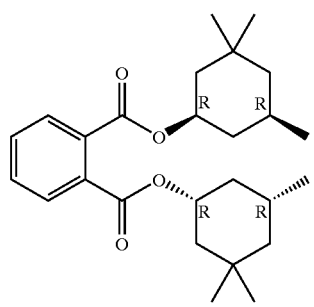

(2)

The present invention provides, in yet another aspect, an optically active bis(cis-3,3,5-trimethylcyclohexyl) phthalate represented by following Formula (1) or (2):

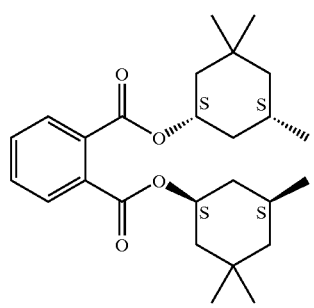

(1)

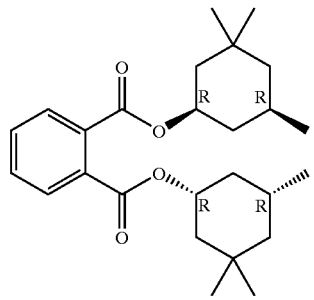

(2)

In another aspect, the present invention provides a process for the preparation of an optically active bis(cis-3,3,5-trimethylcyclohexyl) phthalate, comprising the steps of allowing cis-3,3,5-trimethylcyclohexanol to react with phthalic acid or a reactive derivative thereof and optically resolving the resulting mixture of stereoisomers of bis(cis-3,3,5-trimethylcyclohexyl) phthalate to thereby yield an optically active bis (cis-3,3,5-trimethylcyclohexyl) phthalate represented by Formula (1) or (2).

The present invention provides, in a further aspect, meso-bis(cis-3,3,5-trimethylcyclohexyl) phthalate represented by following Formula (3):

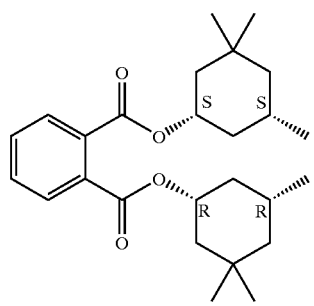

(3)

The present invention provides, in yet another aspect, a thermoplastic resin composition comprising a thermoplastic resin and a solid plasticizer, which solid plasticizer comprises stereoisomers represented by Formulae (1), (2) and (3) and satisfying the following conditions:

$a+b+c=100$, and $50<a+b$ or $50<c$ wherein a, b and c are mole percentages of the stereoisomers represented by Formulae (1), (2) and (3), respectively.

The thermoplastic resin composition may further include a tackifier or may be an aqueous composition including the thermoplastic resin dispersed in water.

In another aspect, the present invention provides a heat-sensitive tacky adhesive comprising the thermoplastic resin composition.

In a further aspect, the present invention provides a heat-sensitive tacky adhesive sheet comprising a base sheet and a tacky. adhesive layer formed at least on one side of the base sheet, which tacky adhesive layer comprises the heat-sensitive tacky adhesive.

In addition and advantageously, the present invention provides a process for producing a heat-sensitive tacky adhesive sheet, comprising the step of applying the heat-sensitive tacky adhesive at least on one side of a base sheet to thereby form a tacky adhesive layer.

In the above formulae, R and S are R,S-expression of configuration and are symbols of rectus and sinister, respectively.

BEST MODE FOR CARRYING OUT THE INVENTION

The bis(cis-3,3,5-trimethylcyclohexyl) phthalate of the present invention comprises three stereoisomers, i.e., bis[(1S,5S)-3,3,5-trimethylcyclohexyl] phthalate represented by Formula (1), bis[(1R,5R)-3,3,5-trimethylcyclohexyl] phthalate represented by Formula (2) and [(1S,5S)-3,3,5-trimethylcyclohexyl][(1R,5R)-3,3,5-trimethylcyclohexyl] phthalate and satisfies the following conditions:

$a+b+c=100$, and $50<a+b$ or $50<c$

In the above conditions, a, b and c are mole percentages of the stereoisomers represented by Formulae (1), (2) and (3), respectively.

In the present description, a mixture containing bis[(1S,5S)-3,3,5-trimethylcyclohexyl] phthalate represented by Formula (1) and bis[(1R,5R)-3,3,5-trimethylcyclohexyl] phthalate represented by Formula (2) in equal proportions may be referred to as "dl-bis(cis-3,3,5-trimethylcyclohexyl) phthalate", and [(1S,5S)-3,3,5-trimethylcyclohexyl][(1R,5R)-3,3,5-trimethylcyclohexyl] phthalate may be referred to as "meso-bis(cis-3,3,5-trimethylcyclohexyl) phthalate".

When bis(cis-3,3,5-trimethylcyclohexyl) phthalate having a proportion a+b exceeding 50 mol %, preferably exceeding 51 mol %, more preferably exceeding 56 mol %, and typically preferably exceeding 60 mol %, is used as a solid plasticizer for a heat-sensitive tacky adhesive, the compound is molten at a temperature at which the label is applied, can easily plasticize the thermoplastic resin and exhibits markedly improved adhesive strength and blocking resistance, as compared with a bis(cis-3,3,5-trimethylcyclohexyl) phthalate wherein a+b=c=50 mol %.

In contrast, when bis(cis-3,3,5-trimethylcyclohexyl) phthalate having a proportion c equal to or more than 50 mol %, preferably equal to or more than 51 mol %, more preferably equal to or more than 56 mol %, typically preferably equal to or more than 60 mol %, and specifically preferably equal to or more than 80 mol % is used as a solid plasticizer of a heat-sensitive tacky adhesive, the compound is molten with a small quantity of heat, and the resulting tacky adhesive layer becomes homogenous in a short time. The heat-sensitive tacky adhesive thus exhibits improved adhesive strength while sustaining blocking resistance, exhibits improved transparency in the tacky adhesive layer and can sustain high adhesive strength and transparency over a long period of time, as compared with bis(cis-3,3,5-trimethylcyclohexyl) phthalate wherein a+b=c=50 mol %.

The bis(cis-3,3,5-trimethylcyclohexyl) phthalate of the present invention can be prepared by allowing cis-3,3,5-trimethylcyclohexanol to react with phthalic acid or a reactive derivative thereof and purifying the resulting mixture of stereoisomers of bis(cis-3,3,5-trimethylcyclohexyl) phthalate.

Cis-3,3,5-trimethylcyclohexanol for use as a reaction material is generally a mixture containing (1S,5S)-3,3,5-trimethylcyclohexanol represented by following Formula (4) and (1R,5R)-3,3,5-trimethylcyclohexanol represented by following Formula (5) in equal proportions.

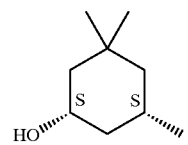

(4)

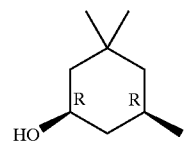

(5)

The proportion of cis-3,3,5-trimethylcyclohexanol in the reaction between cis-3,3,5-trimethylcyclohexanol and phthalic acid or a reactive derivative thereof is from about 1.8 to about 50 folds by mole, preferably from about 1.9 to about 5 folds by mole, and more preferably from about 2.0 to about 2.5 folds by mole that of phthalic acid or a reactive derivative thereof. Cis-3,3,5-trimethylcyclohexanol in excess can also be used as a solvent.

Such reactive derivatives of phthalic acid include, but are not limited to, phthalic anhydride; dimethyl phthalate, diethyl phthalate, diphenyl phthalate and other phthalic esters; phthaloyl dichloride, phthaloyl dibromide and other phthaloyl halides. Among them, phthalic anhydride is preferred.

The concentration of the substrate phthalic acid or a reaction derivative thereof in the reaction system is not specifically limited and is, for example, from about 5% to about 40% by weight and preferably from about 10% to about 30% by weight. A reaction temperature can appropriately be set depending on the type of the substrate and is generally from about −10° C. to about 250° C. and preferably from about 0° C. to about 200° C.

The reaction can be selected from various reactions including dehydration reaction, transesterification reaction and dehydrohalogenation reaction depending on the type of the substrate. For example, when phthalic acid, phthalic anhydride or a phthalic ester is used as the substrate, bis(cis-3,3,5-trimethylcyclohexyl) phthalate is formed by dehydration or transesterification. When phthaloyl chloride or another phthaloyl dihalide is used as the substrate, bis (cis-3,3,5-trimethylcyclohexyl) phthalate is formed by dehydrohalogenation.

The reaction is performed in the presence of, or in the absence of, a solvent. Such solvents include, but are not limited to, solvents that are inert to reaction, such as hexane, heptane, octane, and other aliphatic hydrocarbons; cyclohexane, methylcyclohexane and other alicyclic hydrocarbons; benzene, toluene, xylene, ethylbenzene and other aromatic hydrocarbons; acetic acid, propionic acid, butyric acid, lactic acid, trichloroacetic acid, trifluoroacetic acid and other organic acids; diethyl ether, dibutyl ether, tetrahydrofuran, 1,4-dioxane and other open-chain or cyclic ethers, and other oxygen-containing organic solvents; carbon tetrachloride, chloroform, dichloromethane, 1,2-dichloroethane, dichlorobenzene and other halogenated hydrocarbons; pyridine, picoline, acetonitrile, benzonitrile and other nitrogen-containing organic solvents; esters; ketones; amides; amines; sulfoxides; nitro compounds; and mixtures of these solvents. Among them, hexane, heptane, toluene, xylene, diethyl ether, tetrahydrofuran, chloroform, dichloromethane, 1,2-dichloroethane, pyridine and acetonitrile are preferred.

The reaction may be performed in the presence of a catalyst according to necessity. Such catalysts include, but are not limited to, catalysts generally used in dehydration reaction, transesterification reaction and dehydrohalogenation reaction, such as acid catalysts, base catalysts and neutral catalysts.

Such acid catalysts include, but are not limited to, protonic acids such as inorganic acids (e.g., sulfuric acid, fuming sulfuric acid, sulfuric anhydride, hydrochloric acid, phosphoric acid, fluoroboric acid, hydrofluoric acid, fluorosulfonic acid, chlorosulfonic acid and heteropolyacids) and organic acids (e.g., p-toluenesulfonic acid, benzenesulfonic acid, naphthalenesulfonic acid, methanesulfonic acid, ethanesulfonic acid, trifluoromethanesulfonic acid and other sulfonic acids; chloroacetic acid, trichloroacetic acid, trifluoroacetic acid and other halogenocarboxylic acid, and picric acid). Super strong acids each having a Hammett acidity function $H_0$ of less than −11.93 can also be used as the acid catalyst. Such super strong acids include, for example, $ClSO_3H$—$BF_3$, $FSO_3H$—$BF_3$, $HF$—$NbF_5$, $HF$—$TaF_5$, $SbF_5$, $HF$—$SbF_5$, $SbF_5$—$FSO_3H$, $FSO_3H$—$TaF_5$ and $SbF_5$—$CF_3SO_3H$. In addition, Lewis acids such as $BF_3$, $BF_3OEt_2$, where Et is an ethyl group, $AlCl_3$, $FeCl_3$, $ZnCl_2$, $TiCl_2$, $TiCl_4$, $SnCl_2$, $SnCl_4$ and $MgCl_2$ can also be used as the acid catalyst.

The base catalysts include organic bases and inorganic bases. Such organic bases include, but are not limited to, t-butylamine, t-pentylamine, t-hexylamine, t-octylamine, di-t-butylamine, di-t-pentylamine, di-t-hexylamine, di-t-octylamine, trimethylamine, triethylamine, tributylamine, N-methylpiperidine and other open-chain or cyclic amines; pyridine and other nitrogen-containing heterocyclic compounds; sodium acetate and other carboxylates of alkali metals or alkaline earth metals; sodium methoxide, sodium ethoxide and other alkoxides of alkali metals. Such inorganic bases include, but are not limited to, sodium hydroxide, potassium hydroxide and other hydroxides of alkali metals or alkaline earth metals; sodium carbonate, calcium carbonate and other carbonates of alkali metals or alkaline earth metals; sodium hydrogencarbonate and other hydrogencarbonates of alkali metals; calcium oxide and other oxides of alkaline earth metals.

The neutral catalysts include, but are not limited to, aluminium isopropoxide, titanium isopropoxide and other alkoxides of transition metals.

The amount of the catalyst may at least be an effective amount depending on reaction conditions and is, for example, from about 0.001 to about 100 parts by weight, preferably from about 0.01 to 10 parts by weight and more preferably from about 0.1 to 5 parts by weight, relative to 100 parts by weight of phthalic acid or a reactive derivative thereof.

Solid catalysts, specifically solid acid catalysts, can be used as the catalyst. Such solid acid catalysts include, but are not limited to, strongly acidic ion exchange resins such as non-porous or porous ion exchange resins each containing a sulfonic group; super strongly acidic ion exchange resins such as tetrafluoroethylene polymers containing a sulfonic group; sulfates such as $CaSO_4$, $Fe_2(SO_4)_3$, $CuSO_4$, $NiSO_4$, $Al_2(SO_4)_3$; metal oxides; complex oxides, zeolite and heteropolyacids.

The amount of the solid acid catalyst may at least be an effective amount under reaction conditions and is, for example, from about 0.1 to about 1000 parts by weight and preferably from about 1 to about 100 parts by weight relative to 100 parts by weight of the substrate such a phthalic anhydride. These solid catalysts may be used as a dispersion (a slurry) in the reaction system or may be charged into a column in which the reactants can flow.

The dehydration reaction often uses an acid catalyst, and the transesterification reaction uses a base catalyst or a neutral catalyst, as well as an acid catalyst.

The dehydrohalogenation reaction is performed in the presence of, or in the absence of, a dehydrohalogenating agent. Such dehydrohalogenating agents include, but are not limited to, amines, pyridines, pyrrolidines, amides and inorganic bases. Such amines may be any of primary amines, secondary amines and tertiary amines and include, for example, t-butylamine, t-pentylamine, t-hexylamine, t-octylamine, di-t-butylamine, di-t-pentylamine, di-t-hexylamine, di-t-octylamine, trimethylamine, triethylamine, triethylenediamine, N,N-dimethylaniline and N,N-diethylaniline. Among them, triethylamine and other tertiary amines are preferred. The pyridines include, for example, pyridine and picoline. The amides include, for example, N,N-dimethylformamide and N,N-dimethylacetamide. The inorganic bases include, for example, sodium hydroxide, calcium hydroxide and other hydroxides of alkali metals or alkaline earth metals.

The bis(cis-3,3,5-trimethylcyclohexyl) phthalate of the present invention can be obtained by purifying a mixture of stereoisomers of bis(cis-3,3,5-trimethylcyclohexyl) phthalate prepared by the reaction between cis-3,3,5-trimethylcyclohexanol and phthalic acid or a reactive derivative thereof.

The purification procedures include, for example, extraction, recrystallization (including recrystallization), column chromatography and distillation, of which crystallization is preferred.

The purification procedure by means of crystallization is performed by subjecting the reaction mixture to neutralization, filtration, concentration or another procedure according to necessity, adding a crystallization solvent, and concentrating the resulting solution or decreasing the temperature thereof to thereby precipitate a crystal.

When the reaction is performed in the presence of an acid catalyst, the reaction mixture is often neutralized with a base. Such bases include, but are not limited to, strong bases (e.g., sodium hydroxide, potassium hydroxide and other alkali metal hydroxides), weak bases (e.g., sodium hydrogencarbonate, potassium hydrogencarbonate, sodium carbonate, potassium carbonate, and other carbonates or hydrogencarbonates of alkali metals). The amount of the base can appropriately be set within a range from 0.3 to 10 equivalents to that of the acid catalyst. When a solid catalyst is used as the catalyst, neutralization is not always necessary. For example, the reaction mixture is subjected to, for example, filtration to remove the solid catalyst, the resulting filtrate is concentrated and is then subjected to a crystallization process.

Such crystallization solvents include, but are not limited to, straight- or branched-chain saturated or unsaturated hydrocarbons such as hexane, heptane, octane, cyclohexane, methylcyclohexane and other aliphatic or alicyclic hydrocarbons, as well as benzene, toluene, xylene and other aromatic hydrocarbons; organic acids such as acetic acid, propionic acid, butyric acid, lactic acid, trichloroacetic acid and trifluoroacetic acid; water; alcohols such as methanol, ethanol, propanol, isopropanol, butanol, isobutanol and cyclohexanol; esters such as methyl acetate, ethyl acetate and butyl acetate; ketones such as acetone, diethyl ketone, ethyl methyl ketone, methyl isobutyl ketone, diisobutyl ketone, cyclohexanone, isophorone and 3,3,5-trimethylcyclohexanone; ethers such as diethyl ether, diisopropyl ether, dioxane, tetrahydrofuran and ethylene glycol dimethyl ether; aprotic polar solvents such as amide solvents including dimethylformamide, dimethylacetamide and N-methylpyrrolidone, amine solvents including dimethylaniline, piperazine and piperidine, sulfoxide solvents including dimethyl sulfoxide and sulfolane, nitriles including acetonitrile and benzonitrile, and nitro compounds including nitromethane and nitrobenzene. Each of these solvents can be used alone or in combination.

The amount of the crystallization solvent can appropriately be set in consideration of crystallization efficiency and a target proportion of isomers and is generally such that the solute concentration (the concentration of bis (cis-3,3,5-trimethylcyclohexyl) phthalate) is from about 2% to about 90% by weight and preferably from about 5% to about 50% by weight.

The proportion (abundance ratio) of individual stereoisomers in bis(cis-3,3,5-trimethylcyclohexyl) phthalate of the present invention can be adjusted by appropriately setting, for example, the type of the crystallization solvent, the amount of the crystallization solvent (solute concentration) and crystallization temperature when the compound is purified by recrystallization, and can be adjusted by appropriately setting distillation conditions such as the number of plates and reflux ratio when the compound is purified by distillation.

By such a purification procedure, for example by repeating crystallization operation,
dl-bis(cis-3,3,5-trimethylcyclohexyl) phthalate and meso-bis(cis-3,3,5-trimethylcyclohexyl) phthalate can be isolated, respectively.

The invented bis(cis-3,3,5-trimethylcyclohexyl) phthalate, dl-bis(cis-3,3,5-trimethylcyclohexyl) phthalate and meso-bis(cis-3,3,5-trimethylcyclohexyl) phthalate are useful as additives for delayed tack adhesives (heat-sensitive tacky adhesive), hot-melt adhesives, thermal transfer receiving materials, photosensitizers for color photography, hot-melt ink-jet inks, vibration absorption materials, pencil lead, and vinyl chloride resin compositions, as well as flame retarders, plasticizers, stabilizers or antioxidants for organic polymeric compounds and other organic compounds, lubricating oils and heating media.

The thermoplastic resin composition of the present invention is a thermoplastic resin composition comprising a thermoplastic resin and the invented bis(cis-3,3,5-trimethylcyclohexyl) phthalate as a solid plasticizer.

Such thermoplastic resins include, but are not limited to, homo- or copolymers of (meth)acrylates, styrene-(meth) acrylate copolymers, vinyl chloride- (meth) acrylate copolymers, ethylene- (meth) acrylate copolymers, ethylene-(meth)acrylic acid copolymers, (meth)acrylate-(meth)acrylic acid copolymers, styrene-acrylonitrile-(meth) acrylate copolymers, styrene-(meth)acrylate-(meth)acrylic acid copolymers, styrene-acrylonitrile-(meth)acrylate-(meth)acrylic acid copolymers, ethylene-vinyl acetate-(meth)acrylate copolymers, vinylpyrrolidone-(meth) acrylate copolymers, styrene-butadiene-(meth)acrylate copolymers and other acrylic polymers containing (meth) acrylic acid or its ester as a monomer; vinyl acetate resins, ethylene-vinyl acetate copolymers and other vinyl acetate polymers containing vinyl acetate as a monomer; styrene-butadiene copolymers, isobutylene resins, isobutylene-isoprene copolymers, butadiene resins, styrene-isoprene copolymers, acrylonitrile-butadiene copolymers and other synthetic rubbers; natural rubbers; ethylene-vinyl chloride copolymers, vinyl chloride-vinylidene chloride copolymers, vinylpyrrolidone-styrene copolymers, chlorinated propylene resins, urethane resins and ethyl cellulose. Each of these thermoplastic resins can be used alone or in combination.

Among these thermoplastic resins, acrylic polymers such as those containing a (meth)acrylate as a monomer, vinyl acetate polymers, synthetic rubbers and natural rubbers are preferred. Among the acrylic polymers, typically preferred are acrylate-methacrylate copolymers such as acrylic $C_2$–$C_{20}$ alkyl ester-methacrylic $C_1$–$C_4$ alkyl ester copolymers; acrylate-methacrylate-(meth)acrylic acid copolymers such as acrylic $C_2$–$C_{20}$ alkyl ester-methacrylic $C_1$–$C_4$ alkyl ester-(meth)acrylic acid copolymers; acrylate-styrene-(meth)acrylic acid copolymers such as acrylic $C_2$–$C_{20}$ alkyl ester-styrene-(meth)acrylic acid copolymers, and other acrylic copolymers containing an acrylic ester such as an acrylic $C_2$–$C_{20}$ alkyl ester and a methacrylic ester such as a methacrylic $C_1$–$C_4$ alkyl ester or styrene as comonomers.

The glass transition temperature (Tg) of the thermoplastic resin can appropriately be set depending on the type of the adherend within a range not deteriorating adhesion and blocking resistance of the resulting tacky adhesive sheet and is generally from about –10° C. to about 70° C. and preferably from about 0° C. to about 50° C. A thermoplastic resin having an excessively glass transition temperature may deteriorate the blocking resistance. A thermoplastic resin having an excessively high glass transition temperature may yield an insufficiently formed film of the heat-sensitive tacky adhesive layer upon heating and drying and may deteriorate adhesion The invented bis(cis-3,3,5-trimethylcyclohexyl) phthalate can be used alone as the solid plasticizer, but one or more additional solid plasticizers can be used in combination with the compound in question within ranges not deteriorating the advantages of the present invention.

Such additional solid plasticizers include, but are not limited to, (i) diesters or higher ester compounds (other than the bis(cis-3,3,5-trimethylcyclohexyl) phthalate) of monohydroxy compounds and other hydroxy compounds with dibasic acids and other polybasic acids, (ii) monoesters or higher ester compounds of dihydroxy compounds and other polyhydroxy compounds with organic monobasic acids such as aliphatic, alicyclic or aromatic monocarboxylic acids and (iii) phosphoric esters, phosphites, phosphines and other phosphorus compounds.

Examples of the diesters or higher ester compounds (i) of hydroxy compounds with polybasic acids include dicyclohexyl phthalate (melting point: 63° C.), diphenyl phthalate (melting point: 73° C.), bis(dimethylcyclohexyl) phthalate (melting point: 94° C.), dimenthol phthalate (melting point: 134° C.), dibornyl phthalate (melting point: 136° C.), bis(t-butylcyclohexyl) phthalate (melting point: 103, 150° C.) and other phthalic esters; bis(cis-3,3,5-trimethylcyclohexyl) terephthalate (melting point: 133° C.), bis (trans-3,3,5-trimethylcyclohexyl) terephthalate (melting point: 103° C.), bis (dimethylcyclohexyl) terephthalate (melting point: 89° C.) and other terephthalic esters.

Examples of the ester compounds (ii) of polyhydroxy compounds with organic monobasic acids include sucrose benzoate (melting point: 98° C.) and other carboxylic esters of polyhydric alcohols; hydroquinone diacetate (melting point: 123° C.), trimethylhydroquinone diacetate (melting point: 109° C.), 3,4,5-trimethylcatechol diacetate (melting point: 120° C.) and other diester compounds of hydroquinone or resorcinol which may have a benzene ring substituted with an alkyl group, or catechol which has a benzene ring substituted with an alkyl group with organic monobasic acids.

Examples of phosphoric compounds (iii) include 1,4-cyclohexanedimethanol bis(diphenylphosphate) (melting point: 97° C.), resorcinol bis[di(2,6-dimethylphenyl)phosphate] (melting point: 95° C.), tri(4-methylphenyl) phosphate (melting point: 78° C.), tri(4-t-butylphenyl) phosphite (melting point: 75° C.), triphenylphosphine (melting point: 80° C.) and tri(3-methylphenyl)phosphine (melting point: 100° C.).

When the invented bis(cis-3,3,5-trimethylcyclohexyl) phthalate is used in combination with one or more additional solid plasticizers, the recrystallization of the resulting solid plasticizer is delayed to thereby sustain high transparency and adhesion over a long period of time in many cases. The ratio of the bis(cis-3,3,5-trimethylcyclohexyl) phthalate to the additional solid plasticizers is, for example, from about 1/99 to about 99/1, preferably from about 5/95 to about 95/5 and more preferably about 10/90 to about 90/10.

The content of the solid plasticizer in the thermoplastic resin composition of the present invention is, for example, from about 30 to about 1000 parts by weight, preferably from about 100 to about 1000 parts by weight and more preferably from about 150 to about 900 parts by weight, relative to 100 parts by weight of the thermoplastic resin. If the amount of the solid plasticizer is excessively low, the resulting composition may exhibit insufficient tackiness upon heating. If it is excessively high, the resulting composition may have deteriorated cohesion and may exhibit insufficient adhesive strength.

The thermoplastic resin composition of the present invention may further comprise a tackifier according to necessity. Such tackifier include, but are not limited to, terpene resins, aliphatic petroleum resins, aromatic petroleum resins, cumarone-indene resins, styrenic resins, phenolic resins, terpene-phenol resins, rosin derivatives (e.g., rosin, polymerized rosin, hydrogenated rosin, esters of these rosins with, for example, glycerin or pentaerythritol, and resin acid dimers), xylene resins and other resins. Each of these tackifiers may be used in combination.

The content of the tackifier in the thermoplastic resin composition can appropriately be set depending on the combination of the thermoplastic resin and the solid plasticizer and is preferably from about 10 to about 600 parts by weight and more preferably from about 15 to about 500 parts by weight relative to 100 parts by weight of the thermoplastic resin.

In addition to the tackifiers, the thermoplastic resin composition of the present invention may further comprise conventional additives within ranges not deteriorating the properties of the composition. Such additives include, but are not limited to, film-forming aids, defoaming agents, coatability improvers, thickening agents, lubricants, stabilizers including antioxidants, ultraviolet absorbers and heat stabilizers, antistatic agents, antiblocking agents including inorganic particles and organic particles, and hydrophilic components.

The thermoplastic resin composition of the present invention can be formed into an aqueous composition by dispersing the thermoplastic resin in water using a dispersing agent. Dispersing agents for use herein are not specifically limited and may be any of conventional anionic or nonionic dispersing agents. Such anionic dispersing agents include, but are not limited to, carboxylates, salts of sulfuric esters, sulfonates, and salts of phosphoric esters, of which ammonium salts of carboxylic acids are preferred. Such nonionic dispersing agents include, but are not limited to, polyethylene glycol-based nonionic dispersing agents and polyhydric alcohol-based nonionic dispersing agents.

The aqueous composition can be prepared according to a conventional procedure. For example, the aqueous composition can be prepared by a process in which the components of the thermoplastic resin composition of the present invention are mixed in advance and the resulting mixture is dispersed in water, a process in which the solid plasticizer is dispersed in a thermoplastic resin emulsion or a tackifier emulsion, and the resulting emulsions are then mixed with each other, a process in which the solid plasticizer is dispersed in water in advance and the thermoplastic resin emulsion and the tackifier emulsion are then mixed with the solid plasticizer-water dispersion. The solid plasticizer may be dispersed in the emulsion or water, for example, by dispersing a molten solid plasticizer, by dispersing the solid plasticizer while finely dividing the solid plasticizer, or by dispersing a finely divided solid plasticizer.

The thermoplastic resin emulsion may be prepared by emulsion polymerization or by preparing a polymer according to a procedure other than emulsion polymerization and emulsifying the polymer where necessary using additives. For example, the thermoplastic resin emulsion can be prepared by polymerizing a polymer in the presence of a water-soluble organic solvent (e.g., isopropyl alcohol or another alcohol)., adding additives such as emulsifiers, pH adjusters or acids to the polymer in an organic solvent, adding water to the resulting mixture to yield an emulsion and removing the organic solvent.

The average particle size of the solid plasticizer in the aqueous composition is preferably from about 0.5 to 20 $\mu$m and more preferably from about 1 to about 15 $\mu$m. If the average particle size is less than 0.5 $\mu$m, the resulting composition may exhibit deteriorated blocking resistance, or it may take a long time to pulverize the solid plasticizer to thereby deteriorate productivity. If it exceeds 20 $\mu$m, a surface of the applied composition may be roughened to thereby deteriorate the quality of the resulting label.

The thermoplastic resin composition of the present invention can be used as a heat-sensitive tacky adhesive and can yield a heat-sensitive tacky adhesive sheet by forming a layer of the heat-sensitive tacky adhesive (tacky adhesive layer) at least on one side of a base. The heat-sensitive tacky adhesive layer can be formed by dissolving the heat-sensitive tacky adhesive in an organic solvent and applying the resulting solution or by heating and melting the heat-sensitive tacky adhesive and applying the resulting molten adhesive. The aqueous composition containing the thermoplastic resin dispersed in water can be formed into the heat-sensitive tacky adhesive sheet by applying the composition at least on one side of the substrate and drying the applied composition.

Base materials for use in the heat-sensitive tacky adhesive sheet include, but are not limited to, paper, enamel paper, plastic films, lumbers, cloths, nonwoven fabrics and metals. Polymers constituting such plastic polymers include, but are not limited to, polyethylenes, polypropylenes and other polyolefins; ethylene-vinyl acetate copolymers; poly(vinyl chloride); poly(vinyl chloride-vinyl acetate) copolymers; poly(meth)acrylates; polystyrenes; poly(vinyl alcohol); ethylene-vinyl alcohol copolymers; cellulose acetate and other cellulose derivatives; polyesters such as poly(ethylene terephthalate), poly(butylene terephthalate) and other poly(alkylene terephthalate), poly(ethylene naphthalate), poly(butylene naphthalate) and other poly(alkylene naphthalate); polycarbonates; polyamides such as polyamide 6, polyamide 6/6, polyamide 6/10 and polyamide 6/12; polyester amides; polyethers; polyimides; polyamide imides; and polyether esters, as well as copolymers, blends or crosslinked products of these polymers.

The aqueous composition can be applied, for example, according to procedures using a roll coater, air knife coater, blade coater, rod coater, bar coater, comma coater, gravure coater or silk screen coater. The heat-sensitive tacky adhesive layer can also be formed by printing using, for example, a gravure printing machine. The amount of the heat-sensitive tacky adhesive layer can appropriately be set depending on the application and is, for example, from about 4 to about 20 $g/m^2$ and preferably from about 5 to about 15 $g/m^2$.

The heat-sensitive tacky adhesive sheet can be used as a recording sheet by forming at least one ink absorption layer on the backside of the base.

When the heat-sensitive tacky adhesive sheet comprises an acrylic polymer containing 5 to 50 mol % of a hydrophilic monomer unit as the thermoplastic resin constituting the tacky adhesive layer, it can be used as a recording sheet by means of ink jet process or as a printing sheet (specifically sheet for water based inks) for use in offset printing, flexographic printing and other printing techniques.

When the heat-sensitive tacky adhesive sheet comprises a shrink film as the base, it can be used as a shrink label. Such shrink films include, but are not limited to, uniaxially or biaxially stretched films of poly(vinyl chloride); polyethylenes, polypropylenes and other polyolefins; polystyrenes and other styrenic resins; poly(ethylene terephthalate) and other polyesters; and complexes of these polymers. The thickness of the shrink film is, for example, from about 15 to about 150 $\mu$m and preferably from about 20 to about 120 $\mu$m. A printing layer constituting characters or figures may be formed at least on one side of the shrink film. The shrink label may further comprise a masking layer, a metal deposited layer or another layer between the shrink film and the delayed tack layer (tacky adhesive layer). The shrink label can be used in PET bottles (bottles made of poly(ethylene terephthalate) and other plastic containers, glass containers and metallic containers.

The heat-sensitive tacky adhesive sheet can also be used as a laminating material serving as a protective sheet to protect a sheet-shaped article to be laminated such as photographs and printed matter.

The optically active bis (cis-3,3,5-trimethylcyclohexyl) phthalate of the present invention is bis[(1S,5S)-3,3,5-trimethylcyclohexyl] phthalate represented by Formula (1) or bis[(1R,5R)-3,3,5-trimethylcyclohexyl] phthalate represented by Formula (2). These optically active compounds can be obtained by optically resolving a mixture of stereoisomers of bis(cis-3,3,5-trimethylcyclohexyl) phthalate [or dl-bis(cis-3,3,5-trimethylcyclohexyl) phthalate obtained by purifying the mixture of stereoisomers]. The mixture is obtained by allowing cis-3,3,5-trimethylcyclohexanol to react with phthalic acid or a reactive derivative thereof in the manner as described above.

The optical resolution can be performed according to a conventional technique to obtained an optically active compound from a racemic body. Preferably, the optical resolution is performed by a technique in which the compound is fractionated using an optical resolution column such as CHIRALCEL OD column (available from Daicel Chemical Industries, Ltd.). The optically active bis(cis-3,3,5-trimethylcyclohexyl) phthalate of the present invention is useful as optically resolving agents and intermediate materials for medical drugs and other fine chemicals.

Industrial Applicability

The bis(cis-3,3,5-trimethylcyclohexyl) phthalate, dl-bis(cis-3,3,5-trimethylcyclohexyl) phthalate, meso-bis(cis-3,3,5-trimethylcyclohexyl) phthalate and thermoplastic resin composition of the present invention comprise stereoisomers in a specific proportional range or have a specific three-dimensional structure and can improve adhesive strength and blocking resistance and can further sustain high adhesive strength and transparency, when used in heat-sensitive tacky adhesives.

The heat-sensitive tacky adhesive and heat-sensitive tacky adhesive sheet of the present invention comprise bis(cis-3,3,5-trimethylcyclohexyl) phthalate comprising three isomers in a specific proportional range as a solid plasticizer and have excellent adhesive strength and blocking resistance and can sustain high adhesive strength and transparency.

The present invention also provides a novel optically active bis(cis-3,3,5-trimethylcyclohexyl) phthalate that is useful as, for example, optically resolving agents.

EXAMPLES

The present invention will be illustrated in further detail with reference to several examples below, which are not intended to limit the scope of the invention. Reaction products were analyzed according to the following methods.

Structural Analysis

The structure was analyzed by means of $^{13}$C-NMR (CDCl$_3$) using JNM-A500 NMR measuring device available from JEOL Ltd. and infrared absorption spectrum analysis IR using FTIR-8100M measuring device available from Shimadzu Corporation. The position numbers of carbon atoms in the following $^3$C-NMR structural analysis are as shown in following Formula (6)

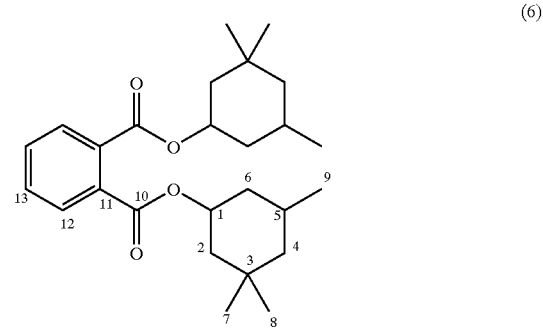

(6)

Measuring Method of Melting Point

About 5 to 10 mg of a sample under test was weighed and placed in a standard aluminium pan, and the melting point of the sample was measured in an atmosphere of nitrogen gas using differential scanning calorimeter (DSC) available from Shimadzu Corporation at a rate of temperature increase of 10° C./min. at temperatures from 25° C. to 150° C.

Analyzing Method of Optical Isomers

Optical isomers were analyzed by using a high performance liquid chromatograph (available from Shimadzu Corporation under the trade name of LC10).

Measuring Conditions

Column: CHIRALCEL OD column (available from Daicel Chemical Industries Ltd.)

Mobile phase: hexane/isopropyl alcohol=250/1

Flow rate: 1.0 ml/min.

Temperature: 25° C.

Detector: UV 210 nm

25 Injected amount: 10 μl (sample concentration: 1.0 mg/ml)

Fractionating Method of Optical Isomers

Optical isomers were fractionated by using a high performance liquid chromatograph (available from Shimadzu Corporation under the trade name of LC10).

Fractionation Conditions

Column: CHIRALCEL OD column 250×Φ10 mm (available from Daicel Chemical Industries Ltd.)

Mobile phase: hexane/isopropyl alcohol=250/1

Flow rate: 4.0 ml/min.

Temperature: 25° C.

Detector: UV 210 nm

Injected amount: 100 μl (sample concentration: 10 mg/ml)

Example 1

In a 2-L glass three-neck flask equipped with an agitating blade, 313 g (2.2 mol) of cis-3,3,5-trimethylcyclohexanol, 148 g (1.0 mol) of phthalic anhydride and 1200 ml of toluene were placed, and the resulting mixture was allowed to react under reflux in the presence of 21 g (0.11 mol) of p-toluenesulfonic acid as a catalyst. A predetermined amount of water formed with a proceeding reaction was distilled off out of the system. The reaction was performed in an atmosphere of nitrogen gas for 6 hours. The conversion from phthalic anhydride was 99.5%. After the completion of reaction, the reaction mixture was neutralized and rinsed with 200 ml of a sodium hydroxide aqueous solution containing 5.84 g (0.15 mol) of NaOH and was further rinsed with 200 ml of water. An organic layer was concentrated and thereby yielded a reaction mixture. To the reaction mixture, a mixture solvent containing 550 ml of methanol and 20 ml of toluene was added as a crystallization solvent, the temperature of the resulting solution was raised to 60° C. to completely solve the solute. The resulting solution was cooled to 20° C. to precipitate crystals, the crystals were filtrated, were rinsed with methanol, were dried and thereby yielded bis(cis-3,3,5-trimethylcyclohexyl) phthalate in a yield of 82%.

The obtained bis(cis-3,3,5-trimethylcyclohexyl) phthalate showed two peaks of melting point at 85° C. and 94° C. in the measurement. The analysis using the optically resolving column reveals the ratio of stereoisomers was such that (a+b)/c=54/46, wherein a, b and c have the same meanings as defined above. Peaks derived from the compound of Formulae (1) and (2) were detected at 10.3 min. and 15.6 min., respectively, and a peak derived from the compound of Formula (3) was detected at 12.1 min. IR analysis shows that an absorption of ester was observed at 1717 $cm^{-1}$.

The results of $^{13}$C-NMR structural analysis show that signals were detected such that 1-position; 72.55 ppm, 3-position; 32.34 ppm, 4-position; 47.57 ppm, 5-position; 27.12 ppm, 7-position (equatorial); 33.06 ppm, 8-position (axial); 25.57 ppm, 9-position; 22.30 ppm, 10-position; 167.05 ppm, 11-position; 132.64 ppm, 12-position; 130.65 ppm, 13-position; 128.74 ppm and were common in the stereoisomers of Formulae (1), (2) and (3), ditto for the following examples and comparative examples. Signals of the 2-position and 6-position of the stereoisomers of Formulae (1) and (2) were observed at 40.24 ppm and 43.85 ppm, respectively. Signals of the 2 position and 6 position of the stereoisomer of Formula (3) were observed at 40.28 ppm and 40.82 ppm, respectively.

Example 2

The procedure of example 1 was repeated, except that 1200 ml of ethanol was used alone instead of the mixture of methanol and toluene and thereby yielded bis(cis-3,3,5-trimethylcyclohexyl) phthalate in a yield of 76%.

The obtained bis(cis-3,3,5-trimethylcyclohexyl) phthalate showed two peaks of melting point at 86° C. and 96° C. in the measurement. The analysis using the optically resolving column reveals the ratio of stereoisomers was such that (a+b)/c=58/42, wherein a, b and c have the same meanings as defined above. Peaks derived from the compounds of Formulae (1) and (2) were detected at 10.3 min. and 15.6 min. and a peak derived from the compound of Formula (3) was detected at 12.1 min. IR analysis shows that an absorption of ester was observed at 1717 $cm^{-1}$.

The results of $^{13}$C-NMR structural analysis show that signals of the 2-position and 6-position of the stereoisomers of Formulae (1) and (2) were observed at 40.24 ppm and 43.85 ppm, respectively and that signals of the 2-position and 6-position of the stereoisomer of Formula (3) were observed at 40.28 ppm and 40.82 ppm, respectively.

Example 3

In a 2-L glass three-neck flask equipped with an agitating blade, 313 g (2.2 mol) of cis-3,3,5-trimethylcyclohexanol, 148 g (1.0 mol) of phthalic anhydride and 1200 ml of cyclohexane were placed, and the resulting mixture was allowed to react under reflux in the presence of 21 g (0.11 mol) of p-toluenesulfonic acid as a catalyst. A predetermined amount of water formed with a proceeding reaction was distilled off out of the system. The reaction was performed in an atmosphere of nitrogen gas for 11 hours. The conversion from phthalic anhydride was 99.1%. After the completion of reaction, the reaction mixture was neutralized and rinsed with 200 ml of a sodium hydroxide aqueous solution containing 5.84 g (0.15 mol) of NaOH and was further rinsed with 200 ml of water. An organic layer was concentrated and thereby yielded a reaction mixture. To the reaction mixture, a solvent mixture containing 300 ml of methanol and 200 ml of cyclohexane was added as a crystallization solvent, the temperature of the resulting solution was raised to 60° C. to completely solve the solute. The resulting solution was cooled to 20° C. to precipitate crystals, the crystals were filtrated, were rinsed with methanol, were dried and thereby yielded bis(cis-3,3,5-trimethylcyclohexyl) phthalate in a yield of 65%.

The obtained bis(cis-3,3,5-trimethylcyclohexyl) phthalate showed two peaks of melting point at 86° C. and 97° C. in the measurement. The analysis using the optically resolving column reveals the ratio of stereoisomers was such that (a+b)/c=62/38, wherein a, b and c have the same meanings as defined above. Peaks derived from the compounds of Formulae (1) and (2) were detected at 10.3 min. and 15.6 min., respectively, and a peak derived from the compound of Formula (3) was detected at 12.1 min. IR analysis shows that an absorption of ester was observed at 1717 cm$^{-1}$.

The results of $^{13}$C-NMR structural analysis show that signals of the 2-position and 6-position of the stereoisomers of Formulae (1) and (2) were observed at 40.24 ppm and 43.85 ppm, respectively and that signals of the 2-position and 6-position of the stereoisomer of Formula (3) were observed at 40.28 ppm and 40.82 ppm, respectively.

Example 4

The procedure of Example 1 was repeated, except that crystallization was performed at a solid concentration of 46% using a solvent mixture containing 420 ml of methanol and 60 ml of toluene. The resulting crystal was further subjected to crystallization three times using a crystallization solvent having the same composition as above and thereby yielded bis(cis-3,3,5-trimethylcyclohexyl) phthalate in a yield of 38%.

The above-prepared bis(cis-3,3,5-trimethylcyclohexyl) phthalate had a melting point of 107° C. Analysis using the optical resolution column reveals that the compound comprises the stereoisomers of Formulae (1) and (2) alone [dl-bis(cis-3,3,5-trimethylcyclohexyl) phthalate]. Peaks derived from the compounds of Formulae (1) and (2) were detected at 10.3 min. and 15.6 min. IR analysis shows that an absorption of ester was observed at 1717 cm$^{-1}$.

The results of $^{13}$C-NMR structural analysis show that signals of the 2-position and 6-position of the stereoisomers of Formulae (1) and (2) were observed at 40.24 ppm and 43.85 ppm, respectively.

Example 5

The procedure of Example 1 was repeated, except that crystallization was performed at a solid concentration of about 11% using 3500 ml of methanol as a crystallization solvent. The filtrate obtained in the crystallization procedure was concentrated and thereby yielded a white crystal. The crystal was further subjected to crystallization with methanol solvent at a solid concentration of 10%, and the resulting filtrate was concentrated and thereby yielded a white crystal. This procedure was repeated three times and thereby yielded bis(cis-3,3,5-trimethylcyclohexyl) phthalate in a yield of 44%.

The above-prepared bis (cis-3,3,5-trimethylcyclohexyl) phthalate had a melting point of 73° C. Analysis using the optical resolution column reveals that the compound comprises the stereoisomer of Formula (3) alone [meso-bis(cis-3,3,5-trimethylcyclohexyl) phthalate].

The results of $^{13}$C-NMR structural analysis show that signals of the 2-position and 6-position of the stereoisomers of Formula (3) were observed at 40.28 ppm and 40.82 ppm, respectively.

Example 6

The procedure of Example 1 was repeated, except that crystallization was performed at a solid concentration of 46% using a solvent mixture containing 420 ml of methanol and 70 ml of toluene as a crystallization solvent. The resulting crystal was further subjected to crystallization twice using a crystallization solvent having the same composition as above and thereby yielded bis(cis-3,3,5-trimethylcyclohexyl) phthalate in a yield of 41%.

The obtained bis(cis-3,3,5-trimethylcyclohexyl) phthalate showed two peaks of melting point at 88° C. and 100° C. in the measurement. The analysis using the optically resolving column reveals the ratio of stereoisomers was such that (a+b)/c=92/8, wherein a, b and c have the same meanings as defined above. Peaks derived from the compounds of Formulae (1) and (2) were detected at 10.3 min. and 15.6 min., respectively, and a peak derived from the compound of Formula (3) was detected at 12.1 min. IR analysis shows that an absorption of ester was observed at 1717 cm$^{-1}$.

The results of $^{13}$C-NMR structural analysis show that signals of the 2-position and 6-position of the stereoisomers of Formulae (1) and (2) were observed at 40.24 ppm and 43.85 ppm, respectively, and that signals of the 2-position and 6-position of the stereoisomer of Formula (3) were observed at 40.28 ppm and 40.82 ppm, respectively.

Among the obtained compounds, a compound corresponding to the peak at 15.6 min. in the optically resolving column analysis was fractionated using an optically resolving column. The resulting white crystal had a melting point of 63.2° C. This crystal was analyzed using an optically resolving column and was found that no peak at a detection time of 12.1 min. (a peak derived from the compound of Formula (3)) and at a detection time of 10.3 min. (a peak derived from the compound of Formula (1) or the compound of Formula (2)) was detected and that a peak at a detection time of 15.6 min. [a peak derived from the compound of Formula (1) or the compound of the Formula (2) (d-bis(cis-3,3,5-trimethylcyclohexyl) phthalate or 1-bis(cis-3,3,5-trimethylcyclohexyl) phthalate)] alone was observed.

The results of $^{13}$C-NMR structural analysis show that signals of the 2-position and 6-position of the stereoisomer of Formulae (1) or the stereoisomer of Formula (2) were observed at 40.24 ppm and 43.85 ppm, respectively.

Comparative Example 1

The procedure of Example 1 was repeated, except that 570 ml of ethanol was used alone as a crystallization solvent, and thereby yielded bis(cis-3,3,5-trimethylcyclohexyl) phthalate in a yield of 80%.

The obtained bis(cis-3,3,5-trimethylcyclohexyl) phthalate showed a peak of melting point at 93° C. in the measurement. The analysis by means of optically resolving column reveals the ratio of stereoisomers was such that (a+b)/c=50/50, wherein a, b and c have the same meanings as defined above. Peaks derived from the compounds of Formulae (1) and (2) were detected at 10.3 min. and 15.6 min., respectively, and a peak derived from the compound of Formula (3) was detected at 12.1 min. IR analysis shows that an absorption of ester was observed at 1717 cm$^{-1}$.

The results of $^{13}$C-NMR structural analysis show that signals of the 2-position and 6-position of the stereoisomers of Formulae (1) and (2) were observed at 40.24 ppm and 43.85 ppm, respectively, and that signals of the 2-position and 6-position of the stereoisomer of Formula (3) were observed at 40.28 ppm and 40.82 ppm, respectively.

Example 7

Preparation of Solid Plasticizer-Water Dispersion

A total of 100 parts by weight of the bis(cis-3,3,5-trimethylcyclohexyl) phthalate [(a+b)/c=54/46] obtained in Example 1 as a solid plasticizer, 15 parts by weight of an anionic surfactant (an ammonium salt of a polycarboxylic acid) as a dispersing agent and 80 parts by weight of water were mixed, the resulting mixture was pulverized in a ball mill to an average particle size of 2.2 μm and thereby yielded a water dispersion of bis(cis-3,3,5-trimethylcyclohexyl) phthalate. The average particle size of the solid plasticizer was determined using a laser scattering particle size distribution analyzer (available from Horiba, Ltd. under the trade name of LA-500) and was indicated by median size.

Preparation of Heat-Sensitive Tacky Adhesive

To the above-prepared water-dispersion of bis(cis-3,3,5-trimethylcyclohexyl) phthalate an aqueous emulsion of a styrene-butadiene-acrylic acid copolymer (glass transition temperature Tg: 20° C.) as a thermoplastic resin, an aqueous dispersion of a hydrogenated terpene resin as a tackifier and water were added, were stirred until the mixture became uniform and thereby yielded a heat-sensitive tacky adhesive having a solid concentration of 54% by weight. The heat-sensitive tacky adhesive contained 35 parts by weight of the thermoplastic resin (styrene-butadiene-acrylic acid copolymer) and 20 parts by weight of the tackifier (hydrogenated terpene resin) relative to 100 parts by weight of the solid plasticizer [bis(cis-3,3,5-trimethylcyclohexyl) phthalate].

Production of Heat-Sensitive Tacky Adhesive Sheet

The above-prepared heat-sensitive tacky adhesive was applied on a body paper side (back side) of a single-sided art paper with a basis weight of 84.9 g/m² and on a surface of a poly(ethylene terephthalate) film (hereinafter briefly referred to as "PET film") 25 μm thick using a bar coater to an amount on dry basis of 12 g/m², the resulting articles were dried at 70° C. for 2 minutes and thereby yielded heat-sensitive tacky adhesive sheets. The surface of the PET film had been subjected to corona discharge treatment,

Example 8

A solid plasticizer-water dispersion and a heat-sensitive tacky adhesive were prepared and heat-sensitive tacky adhesive sheets were produced in the same manner as in Example 7, except that the bis(cis-3,3,5-trimethylcyclohexyl) phthalate [(a+b)/c=58/42] obtained in Example 2 was used as a solid plasticizer.

Example 9

A solid plasticizer-water dispersion and a heat-sensitive tacky adhesive were prepared and heat-sensitive tacky adhesive sheets were produced in the same manner as in Example 7, except that the
bis(cis-3,3,5-trimethylcyclohexyl) phthalate [(a+b)/c=62/38] obtained in Example 3 was used as a solid plasticizer.

Example 10

A solid plasticizer-water dispersion and a heat-sensitive tacky adhesive were prepared and heat-sensitive tacky adhesive sheets were produced in the same manner as in Example 7, except that the bis(cis-3,3,5-trimethylcyclohexyl) phthalate [(a+b)=100 mol %] obtained in Example 4 was used as a solid plasticizer.

Comparative Example 2

A solid plasticizer-water dispersion and a heat-sensitive tacky adhesive were prepared and heat-sensitive tacky adhesive sheets were produced in the same manner as in Example 7, except that the bis(cis-3,3,5-trimethylcyclohexyl) phthalate [(a+b)/c=50/50] obtained in Comparative Example 1 was used as a solid plasticizer.

[0000]

Performance Test 1

The heat-sensitive tacky adhesive sheets obtained in Examples 7 to 10 and Comparative Example 2 were subjected to the following performance tests.

Adhesive Strength

A sample heat-sensitive tacky adhesive sheet on the PET film was cut and thereby yielded a test piece 25 mm wide and 125 mm long. The test piece was heated at 120° C. for 30 seconds to exhibit tackiness, was placed on a glass plate (available from Iwaki Glass under the trade name of Micro Slide Glass HAKUROMUMA) and was attached by a reciprocating motion of a rubber roll under a load of 2 kg. The resulting test piece was left stand at 23° C. at a relative humidity RH of 50% for one day, and the adhesive force (N/25-mm) was determined at a tensile speed of 300 mm/min. at a peel angle of 180° using a tensile strength tester (available from Orientec Co. under the trade name of Tensilon UCT-5T). The results are shown in Table 1.

Blocking Resistance

Four plies of the heat-sensitive tacky adhesive sheet formed on the single-sided art paper were superimposed with each other in such a manner that the glossy surface (right face) of the art paper was in contact with the side (back face) on which the heat-sensitive tacky adhesive was applied, were left stand at 55° C. under a load of 500 gf/cm² (=49 kPa) for 24 hours, and the blocking resistance of the resulting article was determined according to the following criteria. The results are shown in Table 1.

5: The sheets were peeled off from each other without peel resistance.

4: The sheets were peeled off while producing a sound to some degree.

3: The sheets were peeled off while continuously producing a sound.

2: Part of fibers of the paper remained on the tacky adhesive layer upon peeling.

1: The paper was broken due to blocking.

TABLE 1

| | Adhesive Strength (N/25-mm) | Blocking Resistance |
| --- | --- | --- |
| Example 7 | 12.3 | 5 |
| Example 8 | 13.9 | 5 |
| Example 9 | 15.0 | 5 |
| Example 10 | 14.7 | 5 |
| Com. Ex. 2 | 9.6 | 4 |

The results in Table 1 show that the heat-sensitive tacky adhesive sheets according to Examples 7 to 10 have markedly improved adhesive strength and excellent blocking resistance, as compared with the heat-sensitive tacky adhesive sheet according to Comparative Example 2.

Example 11

Preparation of Solid Plasticizer-water Dispersion 1

A total of 100 parts by weight of the bis(cis-3,3,5-trimethylcyclohexyl) phthalate [c=100 mol %] obtained in Example 5 as a solid plasticizer, 15 parts by weight of an anionic surfactant (an ammonium salt of a polycarboxylic acid) as a dispersing agent and 80 parts by weight of water were mixed, the resulting mixture was pulverized in a ball mill to an average particle size of 2.2 μm and thereby yielded a water dispersion of bis(cis-3,3,5-trimethylcyclohexyl) phthalate (solid plasticizer-water dispersion 1). The average particle size of the solid plasticizer was determined using a laser scattering particle size distribution analyzer (available from Horiba, Ltd. under the trade name of LA-500) and was indicated by median size.

Preparation of Solid Plasticizer-Water Dispersion 2

A total of 100 parts by weight of resorcinol bis [di(2,6-dimethylphenyl)phosphate] (melting point: 95° C.) as a solid plasticizer, 15 parts by weight of an anionic surfactant (an ammonium salt of a polycarboxylic acid) as a dispersing agent and 80 parts by weight of water were mixed, the resulting mixture was pulverized in a ball mill to an average particle size of 2.6 μm and thereby yielded a water dispersion of resorcinol bis[di(2,6-dimethylphenyl)phosphate] (solid plasticizer-water dispersion 2).

Preparation of Heat-Sensitive Tacky Adhesive

The above-prepared solid plasticizer-water dispersions 1 and 2 were mixed with each other so that the solid weight ratio of bis(cis-3,3,5-trimethylcyclohexyl) phthalate to resorcinol bis [di(2,6-dimethylphenyl)phosphate] was 50:50 and thereby yielded a solid plasticizer-water dispersion. To this dispersion, an aqueous emulsion of an acrylic polymer (a 2-ethylhexyl acrylate-styrene-acrylic acid copolymer, glass transition temperature Tg: 25° C.) as a thermoplastic resin, an aqueous dispersion of a terpene resin as a tackifier and water were added, were stirred until the mixture became uniform and thereby yielded a heat-sensitive tacky adhesive having a solid concentration of 47% by weight. The heat-sensitive tacky adhesive contained 17 parts by weight of the thermoplastic resin (acrylic polymer) and 26 parts by weight of the tackifier (terpene resin) relative to 100 parts by weight of the solid plasticizer.

Production of Heat-Sensitive Tacky Adhesive Sheet

The above-prepared heat-sensitive tacky adhesive was applied, using a bar coater to an amount on dry basis of 12 g/m, on a body paper side (back side) of a single-sided art paper with a basis weight of 84.9 g/m² and on a surface of a poly(ethylene terephthalate) film (hereinafter briefly referred to as "PET film") 25 μm thick, which surface had been subjected to corona discharge treatment. The resulting articles were dried at 40° C. for 2 minutes and thereby yielded heat-sensitive tacky adhesive sheets.

Comparative Example 3

Preparation of Solid Plasticizer-Water Dispersion 3

A total of 100 parts by weight of dicyclohexyl phthalate (melting point: 65° C.) as a solid plasticizer, 15 parts by weight of an anionic surfactant (an ammonium salt of a polycarboxylic acid) as a dispersing agent and 80 parts by weight of water were mixed, the resulting mixture was pulverized in a ball mill to an average particle size of 2.2 μm and thereby yielded a water dispersion of dicyclohexyl phthalate (solid plasticizer-water dispersion 3).

Preparation of Heat-Sensitive Tacky Adhesive

To the above-prepared dicyclohexyl phthalate-water dispersion (solid plasticizer-water dispersion 3), an aqueous emulsion of an acrylic polymer (a 2-ethylhexyl acrylate-styrene-acrylic acid copolymer, glass transition temperature Tg: 25° C.) as a thermoplastic resin, an aqueous dispersion of a terpene resin as a tackifier and water were added, were stirred until the mixture became uniform and thereby yielded a heat-sensitive tacky adhesive having a solid concentration of 50% by weight. The heat-sensitive tacky adhesive contained 17 parts by weight of the thermoplastic resin (acrylic polymer) and 26 parts by weight of the tackifier (terpene resin) relative to 100 parts by weight of the solid plasticizer (dicyclohexyl phthalate).

Production of Heat-Sensitive Tacky Adhesive Sheet

The above-prepared heat-sensitive tacky adhesive was applied, using a bar coater to an amount on dry basis of 12 g/m², on a body paper side (back side) of a single-sided art paper with a basis weight of 84.9 g/m² and on a surface of a poly(ethylene terephthalate) film (hereinafter briefly referred to as "PET film") 25 μm thick, which surface had been subjected to corona discharge treatment. The resulting articles were dried at 40° C. for 2 minutes and thereby yielded heat-sensitive tacky adhesive sheets.

Performance Test 2

The heat-sensitive tacky adhesive sheets obtained in Example 11 and Comparative Example 3 were subjected to the following performance tests.

Adhesive Strength and Transparency

A sample heat-sensitive tacky adhesive sheet on the PET film was cut and thereby yielded a test piece 25 mm wide and 125 mm long. The test piece was heated at 140° C. for 30 seconds to exhibit tackiness, was placed on a glass plate (available from Iwaki Glass under the trade name of Micro Slide Glass HAKUROMUMA) and was attached by one reciprocating motion of a rubber roll under a load of 2 kg. The resulting test piece was left stand at 23° C. at a relative humidity RH of 50%. The adhesive force (N/25-mm) of the test piece was determined at a tensile speed of 300 mm/min. at a peel angle of 180° using a tensile strength tester (available from Orientec Co. under the trade name of Tensilon UCT-5T) one day, one month and three month into the test. The transparency of the test piece was visually observed. The results are shown in Table 2.

Blocking Resistance

Four plies of the heat-sensitive tacky adhesive sheet formed on the one-side art paper were superimposed with each other in such a manner that the glossy surface (right face) of the art paper was in contact with the side (back face) on which the heat-sensitive tacky adhesive was applied, were left stand at 40° C. under a load of 500 gf/cm² (=49 kPa) for 24 hours, and the blocking resistance of the resulting article was determined according to the following criteria. The results are shown in Table 2.

5: The sheets were peeled off from each other without peel resistance.

4: The sheets were peeled off while producing a sound to some degree.

3: The sheets were peeled off while continuously producing a sound.

2: Part of fibers of the paper remained on the tacky adhesive layer upon peeling.

1: The paper was broken due to blocking.

TABLE 2

| | Adhesive Strength (N/25-mm) | | | Transparency | | | Blocking Resistance |
|---|---|---|---|---|---|---|---|
| | 1 day | 1 month | 3 months | 1 day | 1 month | 3 months | |
| Ex. 11 | 15.7 | 15.3 | 14.9 | transparent | transparent | transparent | 5 |
| Com. Ex. 3 | 9.4 | 0 | 0 | transparent | opaque | opaque | 3 |

The results in Table 2 show that the heat-sensitive tacky adhesive sheet according to Comparative Example 3 became opaque one month into the test due to recrystallization of the solid plasticizer and, in contrast, the heat-sensitive tacky adhesive sheet according to Example 11 sustained high transparency and high adhesive strength even three months into the test and had excellent blocking resistance.

What is claimed is:

1. A composition comprising bis(cis-3,3,5-trimethylcyclohexyl) phthalate comprising stereoisomers represented by the following Formulae (1), (2) and (3) and satisfying the following conditions:

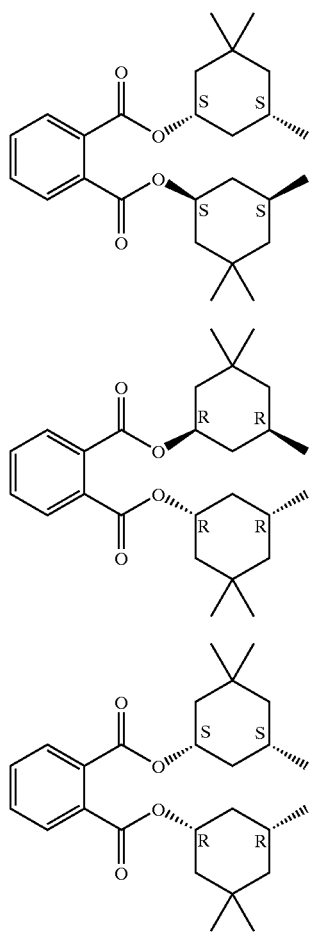

$a + b + c = 100$, and $50 < a + b$ or $50 < c$ wherein a, b and c are mole percentages of the stereoisomers represented by the Formulae (1), (2) and (3), respectively, with the proviso that a solid crystal having a single melting point peak at 93° C. is excluded.

2. A process for the preparation of bis(cis-3,3,5trimethylcyclohexyl) phthalate, comprising the steps of:
allowing cis-3,3,5-trimethylcyclohexanol to react with phthalic acid or a reactive derivative thereof; and
purifying the resulting mixture of stereoisomers of bis(cis-3,3,5-trimethylcyclohexyl) phthalate to thereby yield bis(cis-3,3,5-trimethylcyclohexyl) phthalate comprising stereoisomers represented by the following Formulae (1), (2) and (3) satisfying the following conditions:

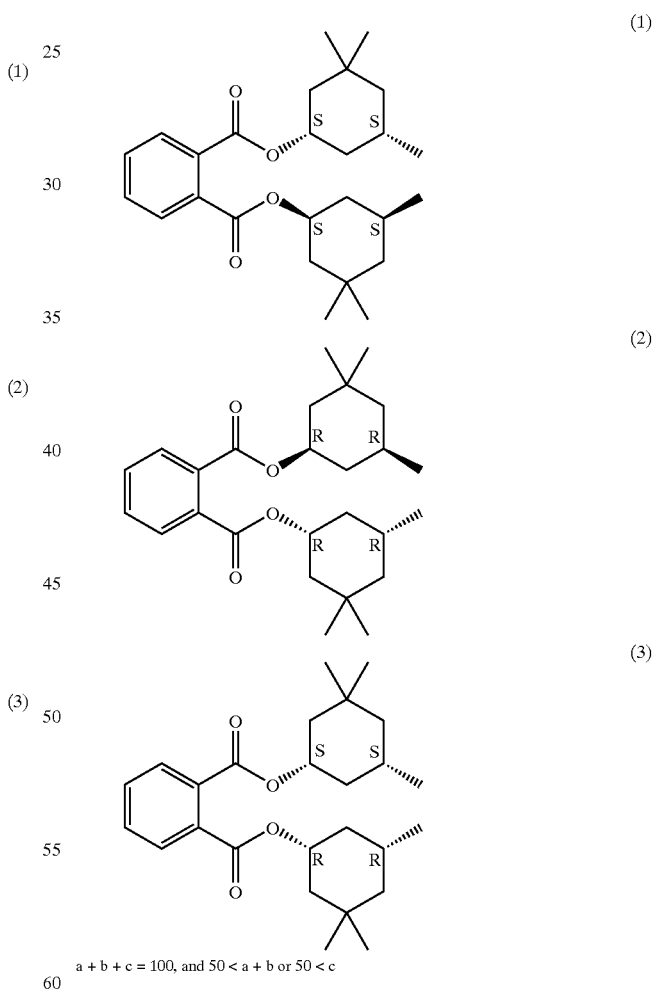

$a + b + c = 100$, and $50 < a + b$ or $50 < c$ wherein a, b and c are mole percentages of the stereoisomers represented by the Formulae (1), (2) and (3), respectively, with the proviso that a solid crystal having a single melting point peak at 93° C. is not obtained.

3. The process for the preparation of bis(cis-3,3,5-trimethylcyclohexyl) phthalate according to claim 2, wherein the mixture of stereoisomers of bis(cis-3,3,5-trimethylcyclohexyl) phthalate is purified by crystallization.

4. A composition comprising purified dl-bis(cis-3,3,5-trimethylcyclohexyl) phthalate comprising a compound represented by the following Formula (1) and a compound represented by the following Formula (2):

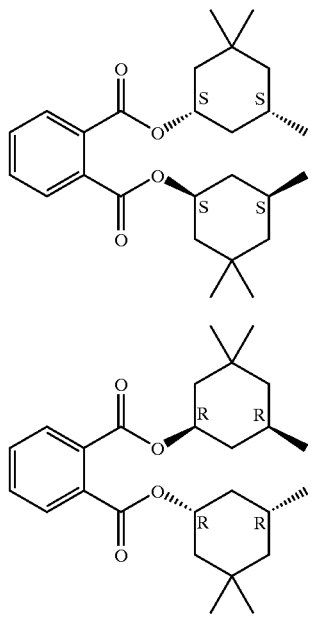

(1)

(2)

with the proviso that the purified dl-bis(cis-3,3,5-trimethylcyclohexyl) phthalate is not a solid crystal having a single melting point peak of 93° C.

5. An optically active and purified bis(cis-3,3,5-trimethylcyclohexyl) phthalate represented by the following Formula (1) or (2):

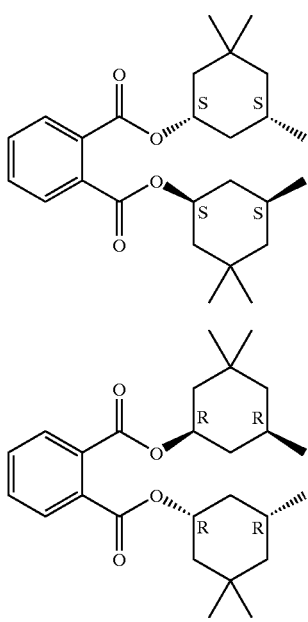

(1)

(2)

with the proviso that the optically active and purified dl-bis(cis-3,3,5-trimethylcyclohexyl) phthalate is not a solid crystal having a single melting point peak of 93° C.

6. A process for the preparation of an optically active bis(cis-3,3,5-trimethylcyclohexyl) phthalate, comprising the steps of:
allowing cis-3,3,5-trimethylcyclohexanol to react with phthalic acid or a reactive derivative thereof; and
optically resolving the resulting mixture of stereoisomers of bis(cis-3,3,5-trimethylcyclohexyl) phthalate to thereby yield an optically active bis(cis-3,3,5-trimethylcyclohexyl) phthalate represented by the following Formula (1) or (2):

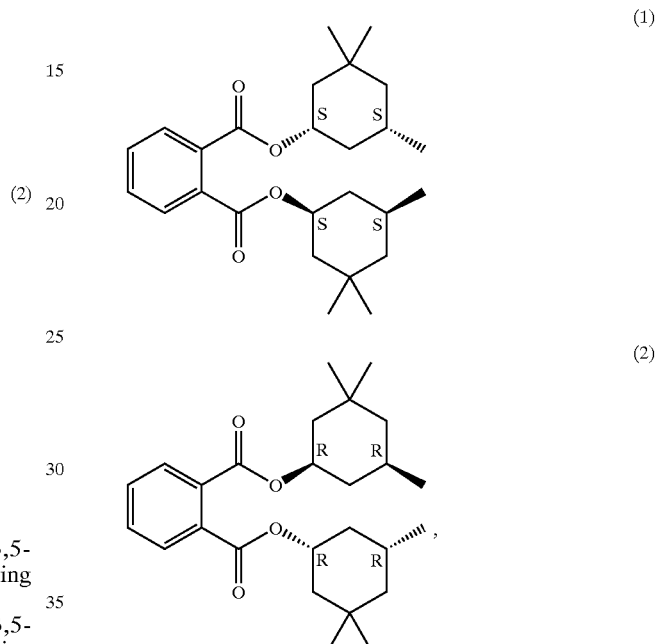

(1)

(2)

with the proviso that a solid crystal having a single melting point peak at 93° C. is not obtained.

7. Purified meso-bis(cis-3,3,5-trimethylcyclohexyl) phthalate represented by the following Formula (3):

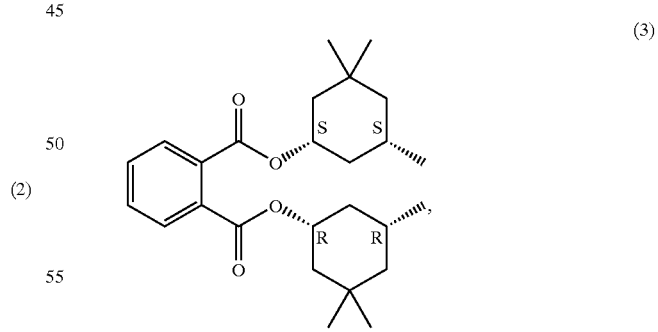

(3)

with the proviso that said purified meso-bis(cis-3,3,5-trimethylcyclohexyl) phthalate is not a solid crystal having a single melting point peak at 93° C.

8. A thermoplastic resin composition, comprising:
a thermoplastic resin; and
a solid plasticizer, the solid plasticizer comprising stereoisomers represented by the following Formulae (1), (2) and (3) and satisfying the following conditions:

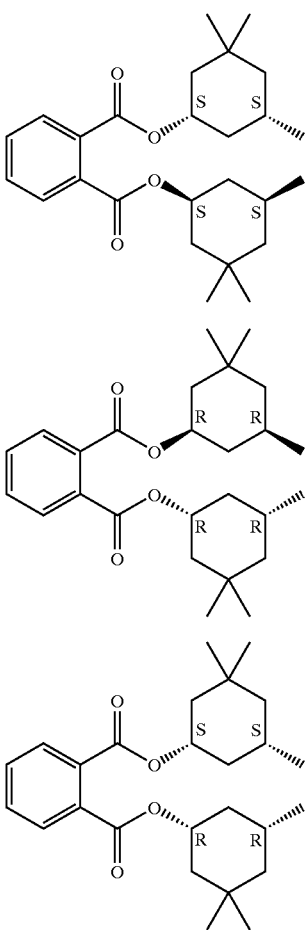

$a + b + c = 100$, and $50 < a + b$ or $50 < c$ wherein a, b and c are mole percentages of the stereoisomers represented by Formulae (1), (2) and (3)1 respectively.

9. The thermoplastic resin composition according to claim 8, further comprising a tackifier.

10. The thermoplastic resin composition according to claim 8 or 9, which is an aqueous composition including the thermoplastic resin dispersed in water.

11. A heat-sensitive tacky adhesive comprising the thermoplastic resin composition as claimed in claim 8 or 9.

12. A heat-sensitive tacky adhesive sheet comprising a base sheet and a tacky adhesive layer formed at least on one side of the base sheet, the tacky adhesive layer comprising the heat-sensitive tacky adhesive as claimed in claim 11.

13. A process for the production of a heat-sensitive tacky adhesive sheet, comprising the step of applying the heat-sensitive tacky adhesive as claimed in claim 11 at least on one side of a base sheet to thereby form a tacky adhesive layer.

14. The composition of claim 1, wherein the proportion of a+b exceeds 51 mol %.

15. The composition of claim 1, wherein the proportion of a+b is equal to or more than 54 mol %.

16. The composition of claim 1, wherein the proportion of a+b is more than 56 mol %.

17. The composition of claim 1, wherein the proportion of a+b is more than 60 mol %.

18. The composition of claim 1, wherein the proportion of c is more than 50%.

19. The composition of claim 1, wherein the proportion of c is more than 51%.

20. The composition of claim 1, wherein the proportion of c is more than 56%.

21. The composition of claim 1, wherein the proportion of c is more than 60%.

22. The composition of claim 1, wherein the proportion of c is more than 80%.

23. The optically active and purified bis(cis-3,3,5-trimethylcyclohexyl) phthalate of claim 5, which has Formula (1).

24. The optically active and purified bis(cis-3,3,5-trimethylcyclohexyl) phthalate of claim 5, which has Formula (2).

25. The composition of claim 8, wherein 50<a+b.

26. The composition of claim 8, wherein 50<c.

* * * * *